United States Patent
Hong

(10) Patent No.: US 6,914,086 B2
(45) Date of Patent: Jul. 5, 2005

(54) CROSSLINKABLE UV ABSORBING AGENT FOR UV ABSORBING LENS

(76) Inventor: Shinn-Gwo Hong, 9F, No. 11, Lane 81, Yuan-Tung Rd., Chungli City (TW)

(*) Notice: Subject to any disclaimer, the term of this patent is extended or adjusted under 35 U.S.C. 154(b) by 27 days.

(21) Appl. No.: 10/603,423

(22) Filed: Jun. 24, 2003

(65) Prior Publication Data
US 2003/0236418 A1 Dec. 25, 2003

(30) Foreign Application Priority Data
Jun. 24, 2002 (TW) .......................... 91113736 A

(51) Int. Cl.$^7$ .............. C08F 2/46; G02C 7/02
(52) U.S. Cl. .............. 522/100; 522/33; 522/34; 522/35; 522/36; 522/46; 522/154; 522/168; 522/170; 522/182; 522/904; 522/905; 523/106; 351/159; 351/160 R
(58) Field of Search ............ 522/33, 34, 35, 522/36, 46, 100, 154, 168, 170, 182, 904, 905; 351/159, 160 R; 523/106

(56) References Cited
U.S. PATENT DOCUMENTS

| | | | | |
|---|---|---|---|---|
| 3,126,676 A | * | 3/1964 | Goldberg et al. ........... | 451/214 |
| 3,429,852 A | * | 2/1969 | Skoultchi .................... | 526/316 |
| 4,395,463 A | * | 7/1983 | Kray .......................... | 428/447 |
| 4,585,693 A | * | 4/1986 | DeBergalis et al. ......... | 428/324 |
| 5,099,027 A | * | 3/1992 | Vogl et al. .................. | 548/259 |

* cited by examiner

*Primary Examiner*—James J. Seidlect
*Assistant Examiner*—Sanza L McClendon

(57) ABSTRACT

A crosslinkable UV absorbing agent prepared by the following steps: (1) preparing a mixture of reactants comprising a UV absorbing compound (A) with multiple pendant hydroxyl groups and an unsaturated monoglycidyl compound (B) with both reactive glycidyl and vinyl groups; (2) mixing a base catalyst (C) with the mixture of reactants; (3) initiating a synthesis reaction of the crosslinkable UV absorbing agent under heating; and (4) recovering the resulting product after the synthesis reaction is completed. The crosslinkable UV absorbing agent is directly applicable in the lens formulation to replace conventional crosslinking agent and UV absorber used in the production of the soft contact lens without any purification or modification.

17 Claims, 2 Drawing Sheets

CROSSLINKABLE UV ABSORBING AGENT FOR UV ABSORBING LENS

BACKGROUND OF THE INVENTION

1. Field of the Invention

The present invention relates to a UV absorbing material with the property of a radical reacted crosslinking agent and the use of such a compound to manufacture UV absorbing soft contact lenses. More particularly, the invention relates to a material having UV absorbing moiety and multiple reactive vinyl groups that can be used to replace conventional crosslinking agents and UV absorbing agents incorporated in the hydrophilic soft contact lenses.

2. The Prior Arts

The UV part of the sunlight that reaches the earth surface consists mostly the radiations with wavelength between about 290 and 400 nm. The UV having short wavelengths below 175 nm is absorbed by oxygen at latitude of about 100 km whereas the radiations between 175 and 290 nm are mostly absorbed by the ozone layers about 15 km above the sea level. However, some UV radiations below 290 nm may still reach the earth surface because of the ozone depletion caused by the environmental pollution. It is well recognized that exposure to ultraviolet radiation is damaging to the cornea and is resulting in ocular pathology. As a result, a great concern is focused on providing adequate ocular protection against UV radiation and protecting people who are liable to UV exposure, for example, patients who have cataract surgery or take photosensitizing drugs.

The addition of UV absorbing compounds in the contact lenses or intraocular lenses to minimize detrimental effect of UV radiation by absorbing UV light in the region of 290 to 400 nm is well known. Many different processes have been disclosed to produce UV absorbing contact lenses or spectacles. For example, the UV absorbing property can be obtained by adding high molecular weight or water insoluable UV absorbing chemicals in lens formulation. However, to prevent leaching of the UV absorber from the lenses during various service environments, the reactive UV absorber that can be copolymerized with the lens material is usually preferred.

In general, lenses are prepared by the free radical polymerization of the lens forming monomers. The constituents in the formulation can be modified to produce lenses with required water content and other physical properties. Copolymerizable UV absorbers are usually directly incorporated in the lens formulation. Methods based on the above process for preparing reactive monomeric UV absorbing compounds can be found in U.S. Pat. Nos. 3,162,676, 3,213,058, 4,304,895, 4,310,650, and 4,528,311. For example, in U.S. Pat. Nos. 4,304,895 and 4,528,311, UV absorbers are functionalized with both UV absorbing moiety and reactive vinyl group that can copolymerize with different acrylic monomers to form contact lenses. Usually, lenses are polymerized in these processes by thermal initiated free radical reaction rather than UV-photo initiated reaction because of the interference of the initiation step by the presence of UV absorbers. Although photo polymerization is also employed in formulations using some of these UV absorbers, a low degree of conversion is usually obtained and the unreacted residual UV absorbing agent in the cured lens must be removed by a subsequent cleaning procedure.

With regard to the thermal initiated process in forming contact lenses, the as-known shortage arises from its relatively long processing cycle that is needed to obtain a lens with a good quality. Consequently, the other alternative-photo polymerization has been proposed to manufacture UV absorbing contact lenses. For example, U.S. Pat. No. 5,098,445 discloses a contact lens with UV absorbing agent covalently bonded after the lens is photo polymerized. The UV absorber is reacted with the hydroxyl group in the formed lens by dipping the lens in an aqueous solution having dissolved halotriazine compound with UV absorbing moiety under alkaline condition. A similar process is also disclosed in U.S. Pat. No. 5,399,692. Yet, it is argued that the triazinyl molecule is detrimental to the physical and optical properties of the lens. Uncertainty in the degree of reaction during the bonding step of halotriazine with the lens materials also arises, which limits the application of the technique.

U.S. Pat. No. 5,914,355 discloses a process to prepare an UV absorbing contact lens after the lens is photo cured. In the process, a derivative of the UV absorbing benzotriazole compound is transformed into a non-UV absorbing material by replacing the hydroxyl group of the phenol moiety with a convertible protective group. This essentially non-UV absorbing agent with reactive vinyl group is added in the lens-forming monomer mixture and photo cured. The formed lens is then changed to be UV absorbing by converting the protective group beck to a hydroxyl moiety in an alkaline environment. This conversion process requires a series of tedious reaction processes. To overcame this shortage, U.S. Pat. No. 5,945,465 discloses a similar process but using the photo-Fries rearrangement to deactivate the protective group during UV exposure. Yet, there are still uncertainties in the degree of conversion in the deactivating step.

U.S. Pat. Nos. 5,681,871 discloses a benzophenone UV absorber with modified reactive anhydride group that can be covalently bonded with the hydroxyl group in the as-formed lens under basic condition. The UV absorbing agent can be applied before or after the lens is photo cured. However, the hydration procedure used to bond anhydride with hydroxyl groups is also relatively time-consuming.

A photo cured UV absorbing agent that required no additional bonding step is disclosed in U.S. Pat. No. 4,719,248. The benzotriazole type UV absorber is modified to have a reactive vinyl group and is claimed to be covalently bonded with the lens-forming monomers by photo polymerization without noticeable yellowness and interference of the curing reaction. Yet a low yield is obtained during the synthesis of the modified UV absorber. In addition, a relatively long photo curing time is required due to the use of photo initiator with active wavelength in the region of visible light.

To obtain a high UV absorption ability, the use of the dual UV absorption compounds that absorb UV in different wavelengths was proposed. In U.S. Pat. No. 4,963,160, a method of bonding two UV compounds with different UV absorbing spectra onto a triazine derivative was proposed. The proposed UV absorption compound requires multiple synthesis procedures to accomplish and needs an additional bonding step to react with the as-formed lens. A similar invention is disclosed in U.S. Pat. No. 6,244,707 in which both benzophenone and benzotriazole derivatives with different UV absorbing power but all containing the mono vinyl group are copolymerized with the lens forming materials to have a strong UV blocking property.

In summary, these UV absorbers usually suffer one or some of the undesired nature such as long reacting time, low conversion, uncertainty in the degree of reaction, leach of unreacted UV absorber, yellowness, inconsistent integrity of the formed lens, expensive reactant used, and tedious reacting process. Henceforth, there exists a need for preparing an improved UV absorbing compound without the aforementioned shortages.

SUMMARY OF THE INVENTION

It is a primary object of the present invention to provide a concise process for preparing a crosslinkable UV absorbing agent for soft contact lenses and overcome the shortages in the prior arts. The resulting product is synthesized by a single step reaction and can also serve as a crosslinking agent without any further modification.

It is another object of the present invention to provide a UV absorbing material that can be covalently bonded to the lens materials through photo polymerization. In addition, the UV absorbing material also acts as a crosslinking agent because of containing multiple reactive vinyl groups so as to make a great mechanical strength of the bonding between the UV absorbing material and lens without the addition of any conventional crosslinking agent.

It is a further object to provide a UV absorbing lens comprising the crosslinkable UV absorbing agent. The crosslinkable UV absorbing agent is needed only by a small amount in the contact lenses to obtain a great UV absorbing effect and exhibits negligible yellowness of the lenses. The bonding between the lens and the UV absorbing material is very stable, and the UV absorbing material does not leach out of the lens. The lens maintains the UV absorbing power after five cycles high temperature aging in the autoclave.

The method for preparing the crosslinkable UV absorbing agent comprises the steps of preparing a mixture of reactants comprising a UV absorbing compound (A) with multiple pendant hydroxyl groups and an unsaturated monoglycidyl compound (B) with both reactive glycidyl and vinyl groups; mixing a base catalyst (C) with the mixture of reactants; Initiating a synthesis reaction of the crosslinkable UV absorbing agent under heat; and recovering the resulting product after the synthesis reaction is completed.

The composition of the reactant compound (A) and (B) can be represented by the following formula:

$$A(B)_n$$

where
- A is a UV absorbing compound originally with multiple pendant hydroxyl groups;
- B is an unsaturated monoglycidyl compound originally with both reactive glycidyl and vinyl groups; and
- n is a number between 1~3, the functionality depending on the reaction of compound (A) and compound (B), and the type of compound (A).

The resulting product is a mixture with different vinyl functional groups and is ready to use without modification.

DETAILED DESCRIPTION BEST MODE FOR CARRYING OUT OF THE INVENTION

Figure 1:
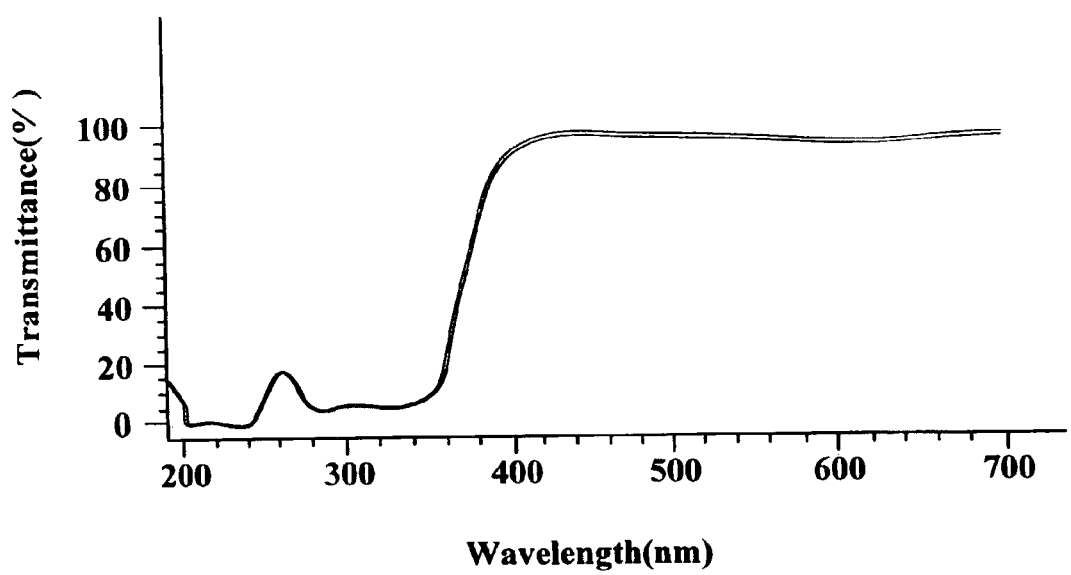
FIG. 1 is a UV-VIS spectra of the lenses comprising 1.25 wt. % of crosslinkable UV absorbing agent UVC2.

The present invention provides a manufacturing process to obtain a crosslinkable UV absorbing agent which is applicable to soft contact lenses, both corrective and non-corrective.

The method of the present invention comprises the steps of: preparing a mixture of the reactants comprising a UV absorbing compound (A) with multiple pendant hydroxyl groups and an unsaturated monoglycidyl compound (B) with both reactive glycidyl and vinyl groups, mixing a base catalyst (C) with the mixture of the reactants; and initiating a synthesis reaction under heat and to recover the resulting product after the synthesis reaction is completed.

The chosen UV absorbing compound (A) has the reactive hydroxyl or amino groups and it has a great absorbance at the wavelengths between 280 and 380 nm. The UV absorbing reactant may be commercially available or be prepared by the conventional techniques known in the field of organic synthesis. The UV absorbing compound (A) is functionalized with more than one reactive vinyl groups by reacting with the second reactant of unsaturated monoglycidyl compound (B) containing both epoxide and vinyl groups to prepare the crosslinkable UV absorbing agent.

The adequate commercial UV absorbing chemicals include different derivatives of triazines, benzotriazoles, and benzophenones containing hydroxyl or amino groups that may be used to react with the epoxide groups in the second reactant of unsaturated monoglycidyl compound (B).

Examples of the benzophenones include 2,4-dihydroxy, 2,2'-dihydroxy, 2,2',4-trihydroxy, 2,2',4,4'-tetrahydroxy, 2,2'-dihydroxy-4,4'-dimethoxy, 4-amino-2-hydroxy-4-methoxy, 4-amino-2,2'-dihydroxy-4-methoxy, 4-amino-2,2'-dihydroxy, and 4-amino-2,2',4'-trihydroxy derivatives of benzophenone.

Examples of the benzotriazoles include 5'-methyl, 3',5'-ditertbutyl, 5'-tertbutyl, 5'-(1,1,3,3-tetramethylbutyl), 5'-ditertbutyl, 3'-secbutyl-5'-tertbutyl, 4'-octoxy, 3',5'-ditertamyl, and 3',5'-bis(α,α-dimethylbenzyl) derivatives of 2-(2'-hydroxyphenyl)benzotriazole; and 2-(2,4-dihydroxyphenyl), 2-(2,5-dihydroxyphenyl), 2-(2,4-dihydroxy-5-chlorophenyl), 2-(2,4-dihydroxy-5-carboxyphenyl), 2-(2,4-dihdroxy-5-carboxymethylphenyl), and 2-(2-hydroxy-5-aminophenyl) derivatives of benzotriazole.

The unsaturated monoglycidyl compound (B) may be glycidyl acrylate, glycidyl methacrylate, or unsaturated monoglycidyl acrylate chemical in the form of:

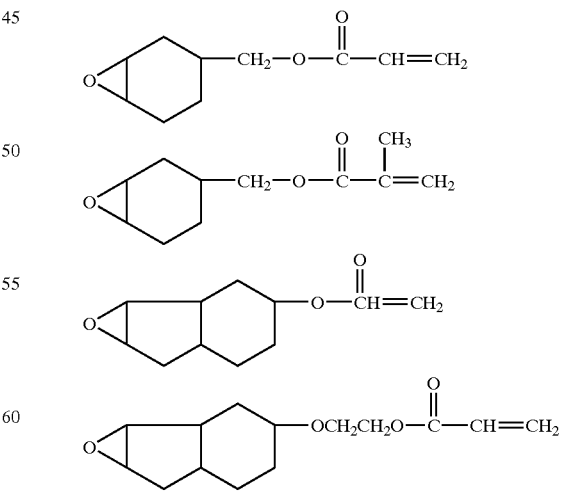

It is important that the UV absorbing compound (A) is well dissolved in the unsaturated monoglycidyl compound (B). A homogeneous liquid mixture containing the two reactants is formed before and after reaction. It is the most important thing that the resulting product after synthesis reaction is completely soluble in the lens forming materials before and after curing. In the aforementioned U.S. Pat. No. 3,162,676, a much less amount of the unsaturated monoglycidyl acrylate was used in the synthesis and was not able to form a homogeneous liquid solution before or after the reaction. The incorporation of inhomogeneous UV absorbing compound in the lens formulation results in a lens with the defects as puddle and overly curved shape. An abundant residual monomer content could also be found in these defected lenses.

In synthesis of the crosslinkable UV absorbing agent, the unsaturated monoglycidyl compound (B) used is in a concentration far excess of the stoichiometric amount over the UV absorbing compound (A), preferably 140 to 250 parts based on the 100 parts of the UV absorbing compound (A). The unsaturated monoglycidyl compound (B) may also be up to 300 parts. The great excess of the unsaturated monoglycidyl compound (B) added ensures the formation of a homogeneous liquid mixture of reactants and lead to a homogeneous liquid crosslinkable UV absorbing product with a high conversion of the UV reactant and a multiple vinyl functional groups after the reaction.

In order to promote the reaction of epoxides (in the reactant of unsaturated monoglycidyl compound (B)) with hydroxyl groups (in the reactant of UV absorbing compound (A)), it needs to use a base catalyst. The base catalyst may be a tertiary amine or an inorganic base, for example, methyl triethyl ammonium chloridem, benzyl trimethyl ammonium bromide, benzyl trimethyl ammonium hydroxide, benzyl triethyl ammonium iodide, benzyl trimethyl ammonium chloride, benzyl triethyl ammonium chloride, benzyl triethyl ammonium bromide, triphenyl phosphine, triphenyl stibine, chromium octanoate, zirconium octanoate, tetramethyl ammonium chloride, tetrabutyl ammonium iodide, tetrabutyl phosphonium bromide, alkaline metal hydroxide (as sodium hydroxide), and salt of the alkaline metal (as sodium bicarbonate). The catalyst is added preferably in the amount of 1 to 6%, based on the weight of the reactant of unsaturated monoglycidyl compound (B).

The use of a polymerization inhibitor is optional to prevent the unwanted premature reaction of the vinyl groups during the synthesis. The inhibitor may be selected from hydroquinone, methyl hydroquinone, hydroquinone monomethyl ether, catechol, and pyrogallol. The amount of a polymerization inhibitor added in the reactants is in the range of 0.02 to 3% by weight, based on the weight of the reactant of unsaturated monoglycidyl compound (B).

In conducting the synthesis, it is important to dissolve the UV absorbing compound (A) in the unsaturated monoglycidyl compound (B) thoroughly before the reaction to avoid the subsequent formation of the inhomogeneous product. Then this liquid reactant mixture is added with desirable amounts of catalyst and inhibitor and sealed in a bottle full with the nitrogen gas. The synthesis is performed at a temperature preferably in the range of 50 to 100° C. for a period preferably in the range of 6 to 24 hours. This process leads to a product with a negligible amount of the unreacted reactant of UV absorbing compound (A).

Upon completion of the synthesis, the result of high performance liquid chromatography (HPLC) and gel permeation chromatography (GPC) analyses reveals that the crosslinkable UV absorbing agent consisting of mixtures of the hydroxy derivatives of the reactant compound (A) with a different amount of substituted acryloxy groups, the oligomers of unsaturated monoglycidyl compound (B) with different chain lengths, and the monomers of reactant of monoglycidyl compound (B). This crosslinkable UV absorbing agent is completely soluble in the lens forming monomer like the hydroxyethylmethacrylate (HEMA). In addition, the synthesized product can be used directly without any further purification or modification with the lens forming materials to manufacture soft contact lenses. Moreover, although the contents of the oligomers and monomers of the monoglycidyl compound (B) in the synthesized compound depend on the dosing amount and the reaction condition, they seldom affect the UV-blocking properties and function of the as-formed lenses. As a result, the great advantage resulting from this great operating window in the synthesis is obtained in the current invention.

The substituted vinyl groups in the as-prepared crosslinkable UV absorbing agent can react with the vinyl groups in the lens forming materials and form covalent bonds through photo initiated free radical polymerization. The crosslinkable UV absorbing agent acts with dual functions of UV absorbing and crosslinking agent due to its UV absorbing moieties and multiple vinyl groups. The soft contact lenses formed using the present invention exhibits great stability during repeated test in autoclave, and the UV blocking power reach the ANSI-Z80 Class 1 standard. To our knowledge, this is the simplest and the most economic method that can allow the lens to have Class 1 UV absorbing power.

The amount of the crosslinkable UV absorbing agent added in the lens is dependent on the lens formulation and the required UV blocking power, preferably in the range of 0.5 to 3.0%, based on the weight of the lens forming materials. Any deviation from the aforementioned range is undesirable because the lens could not have enough UV blocking ability if the amount added is less than 0.5%. Conversely, the added amount exceeding 3.0% could result in lenses having incomplete cure, puddles, curving shapes, or yellowness.

Having been fully described the present invention, examples illustrating its practice are set forth below. These examples should not, however, be considered to limit the scope of the invention, which is defined by the appended claims.

EXAMPLE 1

Preparation of Crosslinkable UV Absorbing Agent

A mixture of 100 parts 2,2',4,4'-tetrahydroxy benzophenone, 150 parts glycidyl methacrylate, 3 parts benzyl triethyl ammonium chloride, and 3 parts hydroquinone monomethyl ether is well mixed in a ball-mill (Retsch, Model: S-100), sealed under nitrogen, and heated in an oil bath at 90° C. for 8 hours. The reactants were purified with the common methods as recrystallization and vacuum distillation before the reaction. A homogeneous viscous liquid product is obtained after completion of the reaction. The results of HPLC and GPC analyses indicated that the product is a mixture of derivatives of hydroxy benzophenones with a different amount of substituted acryloxy groups, oligomers of unsaturated monoglycidyl acrylate reactant with different chain lengths, and monomers of monoglycidyl acrylate reactant but containing a negligible amount of unreacted 2,2',4,4'-tetrahydroxy benzophenone. To test the solubility, the UV absorbing product obtained is added to the HEMA monomer in the amount of 1, 2, and 3 weight % separately and well mixed. In the solubility test, all HEMA solutions containing different amounts of the product show a clear and transparent appearance, which indicates the reacted compound is well soluble in HEMA. The prepared product is referred to as UVC 1.

EXAMPLE 2

Preparation of Crosslinkable UV Absorbing Agent

A mixture of 100 parts 2,2',4,4'-tetrahydroxy benzophenone, 200 parts glycidyl methacrylate, 3 parts benzyl triethyl ammonium chloride, and 3 parts hydroquinone monomethyl ether is well mixed, sealed under nitrogen, and heated in an oil bath at 90° C. for 8 hours. A homogeneous viscous liquid product is obtained after completion of the reaction. The results of HPLC and GPC analyses indicate that the product is also a mixture similar to UVC1 and containing a negligible amount of unreacted 2,2',4,4'-tetrahydroxy benzophenone. This product is also soluble in HEMA and referred to as UVC 2.

EXAMPLE 3

Preparation of the UV Blocking Soft Contact Lenses

The basic formulation to prepare the soft contact lenses constitutes 100 parts HEMA, 32 parts N-vinyl pyrrolidone, 0.75 part 2-chlorothioxanthone, 0.075 part modified Levafix Blue E-BRA (a modified reactive tinting dye), and 75 parts glycerin. The photo initiator with a good light absorbing power within the wavelength range of 380–410 nm is preferred to avoid the interference from the added crosslinkable UV absorbing agent. The formulation was added with two different amounts (1.25 and 2.50 weight %) of as-prepared UVC agent and mixed under reduced pressure. Then the mixture is placed in the preformed polystyrene mold with a diameter of 12.66 mm, a base curve of 8.625, a central lens thickness of 110 microns, and the power of 100. Curing is performed at 60° C. under a light source consisting of 15 watt UV lamps (wavelength 300–410 nm) for 15 minutes. The total accumulated light energy during curing is 2100 mJ/cm$^2$. After curing, the lens is demolded, rinsed with the hot water of 80° C. for 20 minutes to remove the inert glycerin diluent and unreacted residual constituents, and then hydrated with a standard saline at 25° C. for 24 hours.

Figure 2:
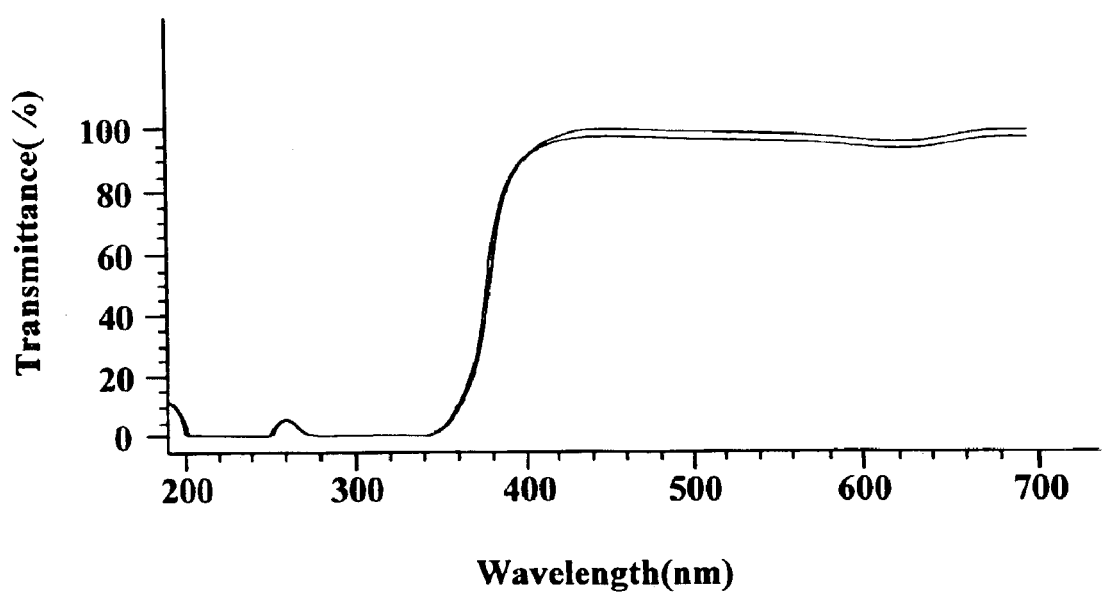
FIG. 2 is a UV-VIS spectra of the lenses comprising 2.5 wt. % of crosslinkable UV absorbing agent UVC2.

The UV absorbance of the lenses is analyzed with a Perkin-Elmer UV-VIS 8453 spectrophotometer before and after autoclave aging. The lens is hold in a quartz cuvette filled with saline. The autoclave is operated at 121° C. and 2 atm. One cycle of autoclave takes about 30 minutes. The UV-VIS spectra are obtained at 1 nm resolution from 190 to 1100 nm. The test results are listed in Table 1. The representative UV-VIS spectra are shown in FIGS. 1 and 2.

The tensile properties of the lens are measured using Instron at a strain rate of 50 mm/min. The specimen with the desired size and shape was die-cut from the cured lens and the cross sectional area of the specimen was measured. The tensile strength measured is also shown in Table 1.

As previously described, a long curing time or a low conversion of the UV absorber is usually obtained when the lens formulations containing the UV absorbing compound are photo cured. However, these shortages are absent in the current invention. From the great physical properties obtained from the cured lens shown in Table 1, the photo initiator and the photo curing process are proven to be adequate for the formulations tested in the invention. This is also a great advantage of using this invention to manufacture UV absorbing soft contact lenses.

TABLE 1

The Characteristic Properties of Lenses Comprising Crosslinkable UV Absorbing Agent

| Lens Characteristics | 1.25 wt. % UVC 1 | 2.50 wt. % UVC 1 | 1.25 wt. % UVC 2 | 2.50 wt. % UVC 2 |
|---|---|---|---|---|
| UV Transmittance (%, 280–315 nm) | 4.17 ± 0.03 | 0.25 ± 0.01 | 4.79 ± 0.03 | 0.29 ± 0.01 |
| UV Transmittance (%, 316–380 nm) | 8.52 ± 0.04 | 1.61 ± 0.01 | 17.53 ± 0.05 | 6.49 ± 0.03 |
| UV-blocking power (ANSI-Z80) | Class 2 | Class 1 | Class 2 | Class 1 |
| Tensile Strength (Kg/cm$^2$) | 2.38 ± 0.31# | 2.29 ± 0.43 | 2.37 ± 0.26 | 2.65 ± 0.37 |
| UV-blocking power After Autoclave (ANSI-Z80) | Class 2 | Class 1 | Class 2 | Class 1 |
| Water Content (%) | 57.5 ± 0.4 | 54.8 ± 0.3 | 55.7 ± 0.4 | 53.4 ± 0.4 |
| Lens Diameter (mm) | 14.53 ± 0.04 | 14.32 ± 0.03 | 14.51 ± 0.03 | 14.23 ± 0.02 |

±standard deviation.

What is claimed is:

1. A crosslinkable UV absorbing agent used for making UV-absorbing contact lenses is prepared by the following steps which comprise:
   (a) preparing a mixture comprising a UV absorbing compound (A) with multiple pendant hydroxyl groups and an unsaturated monoglycidyl compound (B) with both reactive glycidyl and vinyl groups;
   (b) mixing a base catalyst (C) with the mixture of step (a);
   (c) initiating a synthesis reaction of the crosslinkable UV absorbing agent under heating; and
   (d) recovering the crosslinkable UV absorbing agent after the synthesis reaction is completed;
   wherein the compound (B) is at least 140 parts based on 100 parts of said compound (A).

2. The crosslinkable UV absorbing agent according to claim 1, wherein the compound (B) is 140 to 300 parts based on 100 parts of said compound (A).

3. The crosslinkable UV absorbing agent according to claim 1, wherein the compound (B) is 140 to 250 parts based on 100 parts of said compound (A).

4. The crosslinkable UV absorbing agent according to claim 1, wherein the base catalyst (C) is 1 to 6% based on the weight of said compound (B).

5. The crosslinkable UV absorbing agent according to claim 1, wherein the heating temperature in step (c) is 50 to 100° C.

6. The crosslinkable UV absorbing agent according to claim 1, wherein the compound (A) is selected from a group consisting of triazines, benzotriazoles, and benzophenones.

7. The crosslinkable UV absorbing agent according to claim 1, wherein the compound (A) is selected from a group consisting of 5'-methyl, 3',5'-ditertbutyl, 5'-tertbutyl, 5'-(1,1,3,3-tetramethylbutyl), 5'-ditertbutyl, 3'-secbutyl-5'-tertbutyl, 4'-octoxy, 3',5'-ditertamyl, and 3',5'-bis(α,α-dimethylbenzyl) derivatives of 2-(2'-hydroxyphenyl) benzotriazole; 2-(2,4-dihydroxyphenyl), 2-(2,5-dihydroxyphenyl), 2-(2,4-dihydroxy-5-chlorophenyl), 2-(2,4-dihydroxy-5-carboxyphenyl), 2-(2,4-dihydroxy-5-carboxymethylphenyl), and 2-(2-hydroxy-5-aminophenyl) derivatives of benzotriazole; and 2,4-dihydroxy, 2,2'-dihydroxy, 2,2',4-trihydroxy, 2,2',4,4'-tetrahydroxy, 2,2'- dihydroxy-4,4'-dimethoxy, 4-amino-2-hydroxy-4-methoxy, 4-amino-2,2'-dihydroxy-4-methoxy, 4-amino-2,2'-dihydroxy, and 4-amino-2,2',4'-trihydroxy derivatives of benzophenone.

8. The crosslinkable UV absorbing agent according to claim 1, wherein the compound (A) is 2,2'-4,4'-tetrahydroxy benzophenone.

9. The crosslinkable UV absorbing agent according to claim 1, wherein the compound (B) is selected from a group consisting of glycidyl acrylate, glycidyl methacrylate, and unsaturated monoglycidyl acrylate.

10. The crosslinkable UV absorbing agent according in claim 1, wherein the compound (B) is glycidyl methacrylate.

11. The crosslinkable UV absorbing agent according to claim 1, wherein the base catalyst (C) is selected from a group consisting of tertiary amines and inorganic bases.

12. The crosslinkable UV absorbing agent according to claim 1, wherein the base catalyst (C) is selected from a group consisting of methyl trimethyl ammonium chloride, benzyl trimethyl ammonium bromide, benzyl trimethyl ammonium hydroxide, benzyl trimethyl ammonium iodide, benzyl trimethyl ammonium chloride, benzyl triethyl ammonium chloride, benzyl triethyl ammonium bromide, triphenyl phosphine, triphenyl stibine, chromium octanoate, zirconium octanoate, tetramethyl ammonium chloride, tetrabutyl ammonium iodide, tetrabutyl phosphonium bromide, alkaline metal hydroxide, and salt of the alkaline metal.

13. The crosslinkable UV absorbing agent according to claim 1, wherein the base catalyst (C) is benzyl triethyl ammonium chloride.

14. The crosslinkable UV absorbing agent according to claim 1, further comprising a step of adding a polymerization inhibitor before initiating the synthesis reaction.

15. The crosslinkable UV absorbing agent according to claim 14, wherein the polymerization inhibitor is 0.02 to 3% based on the weight of said compound (B).

16. The crosslinkable UV absorbing agent to claim 14, wherein the polymerization inhibitor is selected from a group consisting of hydroquinone, methyl hydroquinone, hydroquinone monomethyl ether, catechol, and pyrogallol.

17. A UV absorbing lens comprising a crosslinkable UV absorbing agent of claim 1.

* * * * *